US006333175B1

(12) United States Patent
Glockshuber et al.

(10) Patent No.: US 6,333,175 B1
(45) Date of Patent: Dec. 25, 2001

(54) YIELD WHEN DISULFIDE-BONDED PROTEINS ARE SECRETED

(75) Inventors: Rudolf Glockshuber, Adlmannstein; Martina Wunderlich, Regensburg; Arne Skerra, Wiesbaden; Rainer Rudolph, Weilheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 08/097,621

(22) Filed: Jul. 27, 1993

Related U.S. Application Data

(63) Continuation of application No. 07/873,963, filed on Apr. 24, 1992, now abandoned.

(30) Foreign Application Priority Data

Apr. 26, 1991 (DE) ................................................ 41 13 750

(51) Int. Cl.⁷ ....................................................... C12P 21/04
(52) U.S. Cl. ........................ 435/71.2; 435/69.1; 435/71.1; 435/471
(58) Field of Search .................................. 435/188, 244, 435/252.33, 69.1, 71.1, 71.2, 471

(56) References Cited

U.S. PATENT DOCUMENTS 4,904,602 * 2/1990 Piget et al. ............................ 435/191

FOREIGN PATENT DOCUMENTS 0 293 793   12/1988  (EP) .
0 315 782    5/1989  (EP) .
0 393 725   10/1990  (EP) .

OTHER PUBLICATIONS

Bowden et. al, 1990, J. Biol. Chem, 265(28) 16760–16766.*
Gilbert et . al. 1990, In–vol. 63, Adv. In. Enzymol. pp. 69–172, John Wiley Interscience, New York.*
Bardwell et al. 1991, Cell, (67) 581–589.*
Bowden et al., "Folding and Aggregation of β–Lactamase in the Periplasmic Space of Escherichia coli", The Journal of Biological Chemistry, vol. 265, No. 28, Issue of Oct. 5, pp. 16760–16766, 1990.

* cited by examiner

Primary Examiner—Remy Yucel
(74) Attorney, Agent, or Firm—Arent Fox Kintner Plotkin & Kahn, PLLC

(57) ABSTRACT

The invention concerns a process for increasing the formation of the natural protein conformation when disulfide-bonded proteins are secreted by a prokaryotic host organism that contains a recombinant DNA coding for the secreted protein whereby the host organism is cultured in a suitable culture medium under suitable conditions for the expression of the recombinant DNA, which is characterized in that a culture medium containing 0.1 to 20 mmol/l of one or several thiol reagents is used.

28 Claims, 2 Drawing Sheets

Expression plasmid pRBIa1-PDI

YIELD WHEN DISULFIDE-BONDED PROTEINS ARE SECRETED

This application is a continuation division of application Ser. No. 07/873,963 filed Apr. 24, 1992, now abandoned.

DESCRIPTION

The present invention concerns a process for increasing the formation of the natural protein conformation when disulfide-bonded proteins are secreted by a prokaryotic host organism that contains a recombinant DNA coding for the secreted protein.

Protein synthesis or translation in prokaryotic microorganisms occurs at the ribosomes in the cytoplasm. When recombinant DNA is expressed in bacterial host organisms it is often desirable that the resulting recombinant gene product or protein is secreted from the cytoplasm through the inner bacterial membrane into the periplasmatic space between the inner and outer membrane. The secreted proteins can then for example be released from the periplasm into the culture medium by an osmotic shock. A disadvantage of this process is that when disulfide-bonded proteins are secreted the native or natural conformation is not usually formed correctly i.e. polypeptides are produced with a false or incomplete formation of the disulphide bridges which are biologically inactive.

Thiol reagents are used in methods for the in vitro renaturation of insoluble proteins which form as inclusion bodies in the cytoplasm when recombinant DNA is expressed in prokaryotic cells. It is known that the thiol reagents are rapidly oxidized to disulphides in the presence of atmospheric oxygen.

An object of the present invention was to increase the formation of the natural protein conformation when disulfide-bonded proteins are secreted.

In particular promoting the formation of the native protein conformation could replace the in vitro renaturation of falsely disulfide-bonded proteins which can be very complicated.

The object according to the present invention is achieved by a process for increasing the formation of the natural protein conformation when disulfide-bonded proteins are secreted by a prokaryotic host organism that contains a recombinant DNA coding for the secreted protein, wherein the host organism is cultured in a suitable culture medium under conditions suitable for the expression of the recombinant DNA whereby the process is characterized in that a culture medium containing 0.1 to 20 mmol/l of one or several thiol reagents is used.

Surprisingly it is possible by using the process according to the present invention to increase the yield of correctly disulfide-bonded proteins by adding thiol reagents to the fermentation medium. The process according to the present invention can be used for all proteins which contain one or several disulphide bridges. In particular when only a small amount of protein is required, e.g. in the production of growth factors on a mg scale (nerve growth factor, interleukins or similar compounds), an in vitro renaturation can be dispensed with by using the process according to the present invention.

A culture medium containing 0.1 to 20 mmol/l of one or several thiol reagents has proven to be suitable for the process according to the present invention. If a culture medium is used which contains less than 0.1 mmol/l of thiol reagents then no appreciable increase in the formation of the natural protein conformation is found. The upper limit for the thiol concentration is about 20 mmol/l and is manifested by a substantial decrease in the yields of secreted functional protein as well as in a marked decline in cell growth. The culture medium used preferably contains 1 to 15 mmol/l and particularly preferably contains 3 to 12 mmol/l of one or several thiol reagents. If glutathione is used as the thiol reagent then about 5 mmol/l has proven to be an optimal concentration.

The term "thiol reagent" used in the present description means either a reducing thiol reagent with SH groups or a mixture of reducing thiol reagents with SH groups and oxidizing thiol reagents with disulfide groups.

Those which have a single SH group per molecule have proven to be particularly suitable as reducing thiol reagents. Particularly preferred substances are reduced glutathione (GSH), cysteine, N-acetylcysteine, cysteamine, β-mercaptoethanol and similar compounds. Most preferred are N-acetylcysteine and reduced glutathione (GSH). The thiol reagents can either be used singly or in mixtures.

Although the sole use of reducing thiol reagents is generally preferred, the use of a mixture of reducing and oxidizing thiol reagents leads to an improved yield of correctly disulfide-bonded proteins. When such a mixture of reducing and oxidizing thiol reagents is used the molar ratio of reducing to oxidizing thiol reagents is preferably 2:1 to 20:1, particularly preferably 5:1 to 10:1. A mixture of a reduced and of an oxidized thiol reagent is for example reduced glutathione (GSH) and glutathione disulfide (GSSG).

An example of the process according to the present invention is the heterologous expression of the bifunctional α-amylase/trypsin inhibitor from Eleusine coracana Gaertneri (RBI) in $E.\ coli$. The inhibitor was characterized by Shivaraj and Pattabiraman (Shivaraj B. & Pattabiraman, T. N., Indian J.Biochem.Biophys. 17 (1980), 181–193; Shivaraj B. & Pattabiraman, T. N., Biochem.J. 193 (1981), 29–36). The amino acid sequence of the inhibitor was disclosed by Campos and Richardson (Campos, F. A. P. & Richardson, M., FEBS Letters 152 (1983), 300–304). This protein is comprised of 122 amino acids, it contains 5 intramolecular disulfide bridges and belongs to a new a-amylase/trypsin inhibitor class (Halford et al., Biochim. Biophys. Acta 950 (1988), 435–440), whereby it is its only bifunctional member. At this point it should, however, be noted that the process according to the present invention can also be applied to the isolation of other secreted recombinant disulfide-bonded proteins (e.g. antibody fragments) in prokaryotic host organisms.

In order to isolate the secretory RBI protein in a functional form in $E.\ coli$ a synthetic RBI gene was fused using genetic engineering methods to the signal sequence of the outer membrane protein A (OmpA) of $E.\ coli$ and the fusion was expressed in $E.\ coli$ on a recombinant plasmid under the control of a lac promoter. In this way the polypeptide chain of the recombinant protein is transported into the periplasm of the prokaryotic host cell where, after cleavage of the signal sequence, it can as a result of the oxidizing properties of this cell compartment fold to form the native protein with formation of the intramolecular disulfide bridges. However, only small amounts of the functional protein can be obtained by this folding. When thiol reagents are present in the culture medium according to the present invention it is, however, possible to considerably increase the yield of functional protein (by a factor of 5).

The host organism for the process according to the present invention is a prokaryotic host organism. The expression of the recombinant protein is preferably carried out in a gram-negative prokaryotic host organism, particularly preferably in $E.\ coli$.

In the process according to the present invention it is in general preferable that the recombinant DNA coding for the secreted protein has an operative linkage with a DNA fragment that codes for a signal peptide for penetrating inner bacterial membranes. The term "operative linkage" within the sense of the present invention means that there is a translational fusion between the heterologous protein and the signal peptide. In this process the signal peptide usually forms the N-terminal part of the translational fusion. The type of signal peptide is not critical for the present invention apart from the fact that it should enable the secretion of the recombinant protein. A large number of such signal peptides are known to one skilled in the area of molecular biology. A series of signal peptides are enumerated for example by Winnacker (Gene und Klone, Eine Einfuhrung in die Gentechnologie, published by Chemie Verlag Weinheim (1985), p. 256). If the process according to the present invention is carried out in E. coli as the host organism then the signal peptide from the E. coli OmpA protein has proven to be particularly suitable.

For expression in a prokaryotic host organism the recombinant DNA which codes for the secreted protein must be under the control of an expression signal or promoter recognized by the transcription system of the host. Such expression signals which are active in prokaryotic host cells are known to one skilled in the area of molecular biology. An inducible expression signal is preferably used for the process according to the present invention. Examples of an inducible E. coli promoter are the lac promoter, which can be induced by isopropyl-β-D-galactoside (IPTG), as well as synthetic derivatives of the lac promoter (e.g. the tac or trc promoter).

The recombinant DNA which codes for the secreted disulfide-bonded protein is usually introduced into the prokaryotic host cell by transformation. Techniques for the transformation of different prokaryotic host organisms are known to one skilled in the art and therefore do not need to be mentioned individually. The recombinant DNA present in the transformed host cell is usually on a recombinant vector which can either be present extrachromosomally (e.g. plasmid) or integrated into the genome of the host cell (e.g. bacteriophage λ). A plasmid is preferably used as the vector. It is not critical for the process according to the present invention which particular plasmid is used for this as the expression vector. It is only important that the recombinant DNA coding for the desired protein can be transcribed and translated to an adequate extent by the host cell. The translation product of the recombinant DNA must, however, be present in a form which allows a secretion through the inner bacterial membrane into the periplasm.

As set forth above, a recombinant protein which is fused with a signal sequence is usually transported into the periplasm of a prokaryotic host cell. This also represents a preferred embodiment of the present invention. However, when using certain host strains secretion does not only take place into the periplasm but there is also a massive protein secretion into the culture medium. EP-A 0 338 410 discloses E. coli strains which are capable of such massive protein secretion into the culture medium as well as a process for the production of such strains. The E. coli strains DS410 (DSM 4513) or BW7261 (DSM 5231) mentioned in EP-A 0 338 410 are preferably used as starting strains for the production of these secretor mutants.

A complete medium is preferably used as the culture medium for the process according to the present invention, in particular a medium which contains substances or mixtures of substances from cell extracts. An example of such a medium is the LB medium which contains mixtures of substances from enzymatically digested cell extracts (Bacto-tryptone and yeast extract).

The pH value of the culture medium is preferably in a range between pH 5 and pH 9. The pH value of the culture medium is preferably between 6 and 8. If the LB medium is used as the culture medium then is has proven to be advantageous to adjust the pH value to 7.4 when preparing the medium. The pH value of the medium then decreases during cell growth and experience has shown that it is at about 6.8 in stationary overnight cultures (time of cell harvest).

The process according to the present invention is preferably carried out in a shaking culture in a complete medium. It is, however, also possible to grow the host organisms in a well aerated fermenter or/and in the presence of a minimal medium.

A further embodiment of the process according to the present invention is characterized in that one or several monosaccharides or/and oligosaccharides are added to the culture medium which cannot be metabolized by the prokaryotic host organism used. From a publication by Bowden and Georgiou (J. Biol. Chem. 265 (1990), 16760–16766) it is known that the addition of non-metabolizable sugars can promote the formation of the native protein conformation. The additional use of these non-metabolizable sugars within the scope of the process according to the present invention has a further supporting effect on the formation of the native protein conformation of secreted proteins. Examples of non-metabolizable sugars are for instance sorbose (a monosaccharide), saccharose (a disaccharide) and raffinose (a trisaccharide). It is advantageous for the process according to the present invention that the concentration of the non-metabolizable monosaccharides or/and oligosaccharides in the culture medium is between 0.1 mol/l and 1 mol/l, preferably between 0.3 mol/l and 0.7 mol/l.

A further particularly preferred embodiment of the process according to the present invention comprises an overexpression of a protein disulfide isomerase gene in a host organism together with the expression of the recombinant DNA coding for the secreted disulfide-bonded protein. It is preferable to use a protein disulfide isomerase gene from gram-negative bacterial species, particularly preferably a protein disulfide isomerase gene from E. coli. The DNA sequence of such a gene is shown in SEQ ID NO: 3.

Surprisingly it was ascertained that a coexpression and cosecretion of a host's own protein disulfide isomerase gene in combination with the addition of thiol reagents into the culture medium results in an increase in the yield of functional secreted protein which exceeds the sole effect of the addition of thiol reagents. In contrast the sole coexpression of protein disulfide isomerase (PDI) without addition of thiol reagents does not result in an increase in yield.

The term "overexpression" according to the present invention means an increase in the protein disulfide isomerase expression in comparison to a wild type of the prokaryotic host organism used in a particular case. Such an overexpression can for example be achieved by placing the protein disulfide isomerase gene under the control of a strong, preferably inducible, expression signal (e.g. a lac promoter or derivatives thereof). The overexpression of the PDI gene preferably takes place in "operative linkage" with a signal peptide for the penetration of inner bacterial membranes. The natural PDI signal sequence is particularly preferably used for this purpose.

In an embodiment of the process according to the present invention the recombinant DNA coding for the protein to be secreted and the protein disulfide isomerase gene can for example be present on a single expression vector in the host cell. This expression vector is preferably an extrachromosomal vector i.e. a plasmid, it can, however, also be present integrated into the chromosome of the host cell (e.g. lambda phage). When a single expression vector is used it is preferred that the recombinant DNA and the protein disulfide isomerase gene are under the control of a single expression signal i.e. in the form of a dicistronic operon.

on the other hand it is, however, also possible that the recombinant DNA coding for the protein to be secreted and the protein disulfide isomerase gene are present on two mutually compatible extrachromosomal expression vectors which are each under the control of their own expression signal (promoter).

It is intended to elucidate the present invention further by the following examples in conjunction with FIGS. 1 and 2 as well as SEQ ID NO: 1–5.

Figure 1:
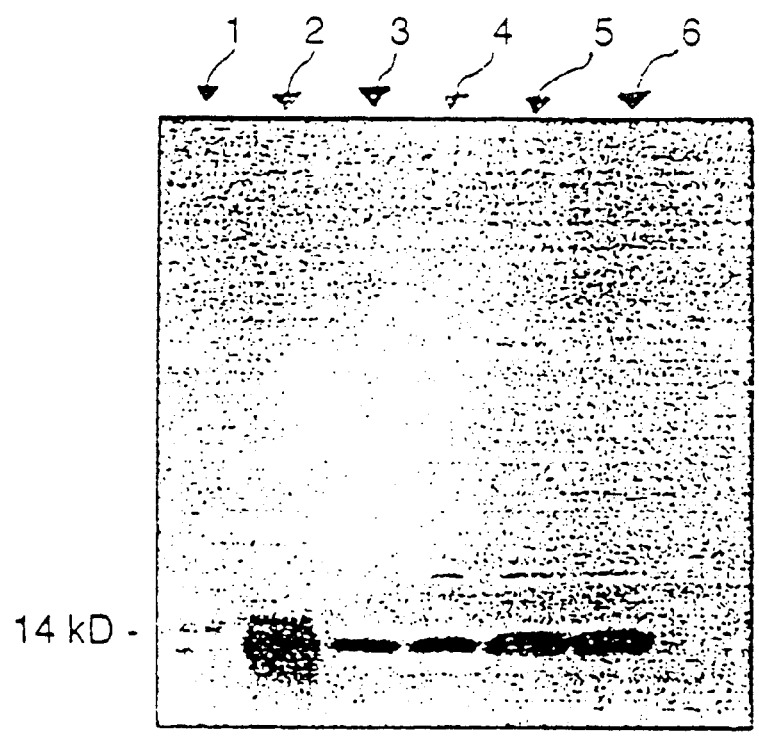
FIG. 1 shows an immunoblot for the detection of soluble processed RBI after addition of different amounts of glutathione to the culture medium.
Figure 2:
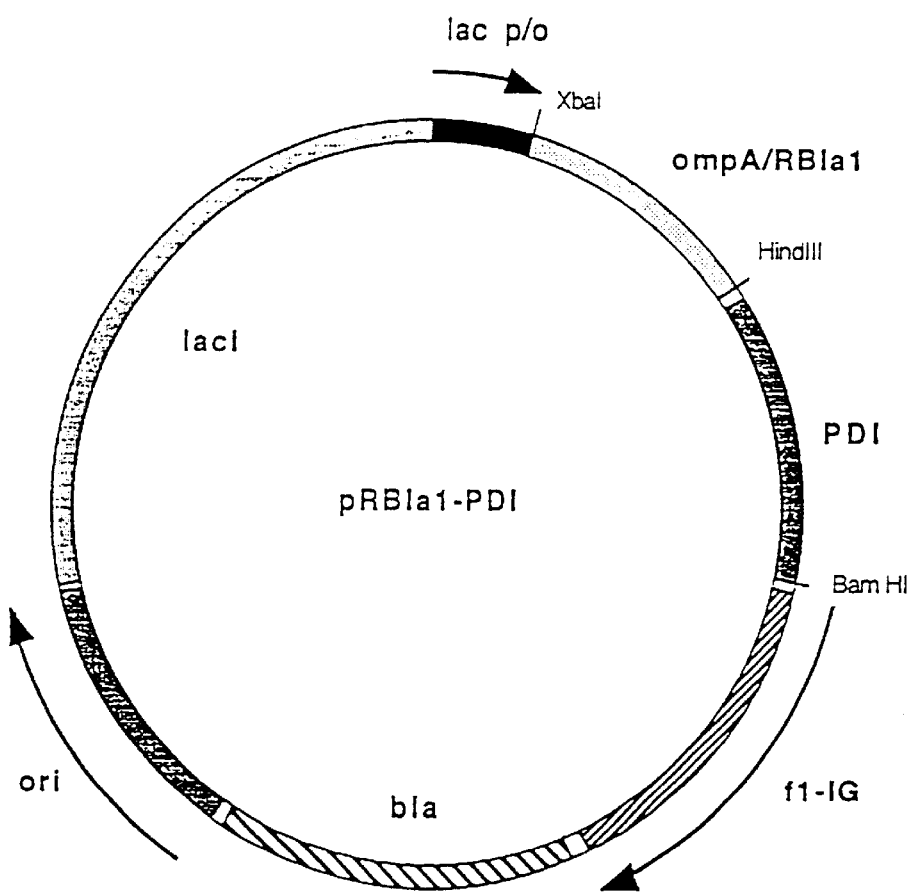
FIG. 2 shows a schematic representation of the expression plasmid pRBIa1-PDI.

SEQ ID NO: 1 shows the DNA sequence of the plasmid pRBIa1-PDI used for the coexpression of RBI and the protein disulfide isomeras (PDI) from E. coli W3110.

SEQ ID NO: 2 shows the sequence of the OmpA/RBI gene. The double-stranded DNA is composed of 14 synthetic oligonucleotides and is bounded by the restriction cleavage sites XbaI and HindIII. The DNA strand shown in the sequence protocol is composed of 7 oligonucleotides which correspond to the following sections:

| 1:bases | 2–62 |
| 2:bases | 63–126 |
| 3:bases | 127–195 |
| 4:bases | 196–258 |
| 5:bases | 259–322 |
| 6:bases | 323–396 |
| 7:bases | 397–455 |

The opposite strand is also formed from 7 oligonucleotides which are complementary to the following sections of the DNA strand shown:

| 8:bases | 6–68 |
| 9:bases | 69–132 |
| 10:bases | 133–201 |
| 11:bases | 202–264 |
| 12:bases | 265–328 |
| 13:bases | 329–402 |
| 14:bases | 403–459. |

SEQ ID NO: 3 shows the sequence of the protein disulfide isomerase gene with the natural signal sequence and ribosomal binding site.

SEQ ID NO: 4 shows the N-terminal primer for the amplification of the PDI gene.

SEQ ID NO: 5 shows the C-terminal primer for the amplification of the PDI gene.

EXAMPLE 1

Gene Synthesis

Preliminary remark:

Molecular genetic techniques were based on Maniatis et al. (Molecular Cloning. A Laboratory Manual (1982), Cold Spring Harbor Laboratory, New York), oligonucleotides were prepared according to the phosphoramidite method (Sinha et al., Nucl. Acids Res. 12 (1984), 4539–4557; Kaplan, B. E., Trends Biotechnol. 3 (1985), 253–256) on an automatic synthesis apparatus type 380A from Applied Biosystems GmbH company.

The synthetic gene which codes for the fusion between the OmpA signal sequence and RBI was composed of 14 synthetic oligonucleotides (SEQ ID NO: 2). The oligonucleotides were purified by polyacrylamide/urea gel electrophoresis and, with the exception of the two protruding oligonucleotides at the 5' and at the 3' end of the gene, were each phosphorylated at their 5' ends. Afterwards all oligonucleotides were combined in equimolar ratios and hybridized and ligated in a single preparation. The gene is bounded by the restriction sites XbaI and HindIII. The amino acids of the OmpA signal sequence are indicated by a negative sign.

EXAMPLE 2

Construction of the expression plasmid pRBIa 1

The synthetic gene obtained according to example 1 was cloned into the expression plasmid pASK40 (Skerra et al., BIO/TECHNOLOGY 9 (1991), 273–278) via the restriction sites XbaI and HindIII. The sequence of the synthetic gene was checked by dideoxy sequencing. The resulting plasmid was denoted pRBIa1.

EXAMPLE 3

Functional expression of RBI in the periplasm of E. coli

A stationary overnight culture of E. coli JM83 (Yannish-Perron et al., Gene 33 (1985), 103–119) which had been transformed with pRBIa1was diluted in a ratio of 1:100 with 2.5 l LB medium (1 l LB medium contains 10 g Bactotrypton (Difco Factories, Detroit, Michigan USA), 5 g yeast extract (Difco Factories) and 5 g NaCl, pH 7.4) containing ampicillin (100 µg/ml) and shaken at 26° C. until an $OD_{550}$ of 1.0 was attained. Afterwards the culture was divided into 9 indentical 250 ml portions, each culture was induced with IPTG (isopropyl-β-D-galactoside; final concentration 1 mmol/l), but different amounts of glutathione (GSH) were added. The cells were shaken further overnight at 26° C. and harvested by centrifugation (Sorvall SS34, 4° C., 5000 rpm, 15 minutes). Afterwards the cells were taken up in 100 mmol/l Tris/HCl pH 7.5, 20 mmol/l Na-EDTA at 4° C. so that in each case cell densities of 200 ($OD_{550}$) were obtained. The cells were subsequently lysed in a french pressure cell press (Aminco) at 18000 PSI. The lysates were centrifuged (Sorvall SS34, 4° C., 15000 rpm, 30 minutes) and the soluble supernatants were tested for their content of soluble functional RBI.

5 µl of each of the soluble supernatants obtained were separated on a 15% polyacrylamide/SDS gel (Fling & Gregerson, Anal. Biochem. 155 (1986) 83–88). The separated proteins were transferred by electro-elution onto a nitrocellulose membrane and the RBI bands were stained immunospecifically with the aid of a rabbit anti-RBI antibody. The immunoblotting was carried out according to Blake et al., Anal. Biochem. 136 (1984), 175–179.

FIG. 1 shows an analysis of the expression yields of soluble RBI by immunoblotting. Lane 1 represents a molecular weight standard. 0.8 µg RBI purified from Eleusine coracana Gaertneri was applied to lane 2. Equivalent amounts of the cell extracts with different amounts of added glutathione were applied to lanes 3 to 6. In lane 3 there was no GSH addition to the culture medium. In lanes 4, 5 and 6, 1 mmol/l, 5 mmol/l and 10 mmol/l GSH was added to the culture medium.

A polyclonal anti-RBI antiserum was used as the antibody which was produced by standard methods (see e.g. Sambrook et al., Molecular Cloning. A Laboratory Manual (1989), Cold Spring Harbor Laboratory Press, chapter 18) by twice immunizing a New Zealand rabbit with purified RBI from Eleusine coracana Gaertneri.

It can be seen from the figure that the addition of GSH increases the intensity of the immunospecifically stained bands. This is particularly apparent at concentrations of 5 mmol/l and 10 mmol/l GSH.

The amount of RBI in the soluble fractions of the cell extracts obtained was determined quantitatively by determining the inhibitory activity with respect to trypsin from bovine pancreas. It could be shown that the amount of intracellular functional inhibitor can be increased up to 5-times compared to the expression without the described additions to the medium (Table 1).

In addition it can be seen from Table 1 that an improvement in the yield of functional inhibitor is also obtained by addition of a mixture of reduced glutathione (GSH) and glutathione disulfide (GSSG).

In all tests carried out 5 μg trypsin from bovine pancreas in 1 ml 100 mmol/l NaCl, 50 mmol/l Tris/HCl pH 8.0, 10 mmol/l $CaCl_2$, 0.005% (v/v) Triton X-100 was incubated with the amount of RBI to be determined for 30 minutes at 25° C. After addition of 20 μl 10 mmol/l N-α-benzoyl-L-arginine-4-nitranilide (chromogenic test substrate) the residual activity of trypsin was determined by recording the timecourse of the increase in absorbance at 405 nm. The inhibitor concentration in the test was determined from the difference between the activity of the free enzyme (without addition of the inhibitor) and the measured residual activity in each case. Table 1 shows the increase in the expression of functional RBI by addition of GSH or a mixture of GSH and GSSG.

TABLE 1

|  | mg/l · OD* | relative increase | mg/l* | relative increase |
|---|---|---|---|---|
| without GSH | 0.07 | 1.0 | 0.36 | 1.0 |
| 5 mmol/l GSH | 0.37 | 5.3 | 1.65 | 4.6 |
| 10 mmol/l GSH | 0.34 | 4.9 | 1.38 | 3.8 |
| 5 mmol/l GSH+ 1 mol/l GSSG | 0.25 | 3.9 | 1.18 | 2.7 |

*The yields of intracellular functional RBI are given in mg/l · OD (liter × optical density), the volume yields are quoted in mg/l.

EXAMPLE 4

Use of N-acetyl-L-cysteine as a further thiol reagent

As described in example 3 cultures of *E. coli* JM83 which had been transformed with the plasmid pRBIa1were propagated at 26° C. in LB medium containing ampicillin (100 μg/ml) and induced with IPTG (final concentration: 1 mmol/l) at an $OD_{550}$=1. N-acetyl-L-cysteine in a solid form (final concentration: 5 and 10 mmol/l) was added at the same time. The cultures were then shaken further overnight and, as described in example 3, tested for their content of functional RBI by the trypsin inhibition test. The results are summarized in Table 2 and show that the concentration range in which the N-acetyl-L-cysteine is active is very similar to that of reduced glutathione.

TABLE 2

Expression of functional RBI by addition of N-acetyl-cysteine

| Addition to the medium | mg/l · OD* | relative increase | mg/l* | relative increase |
|---|---|---|---|---|
| without addition | 0.07 | 1.0 | 0.36 | 1.0 |
| 5 mmol/l N-acetyl-cysteine | 0.31 | 4.4 | 1.27 | 3.5 |
| 10 mmol/l N-acetyl-cysteine | 0.25 | 3.6 | 0.83 | 2.3 |
| 5 mmol/l GSH | 0.37 | 5.3 | 1.65 | 4.6 |

*The yields of intracellular functional RBI are quoted in mg/l · OD, the volume yields in mg/l. The determination of the RBI activity was carried out by the trypsin inhibition test in the soluble fraction of the total cell extract (cf. example 3).

EXAMPLE 5

Coexpression and cosecretion of periplasmatic protein disulfide isomerase (PDI) and simultaneous addition of thiol reagents to the culture medium In order to coexpress the host's own periplasmatic protein disulfide isomerase (PDI), the PDI gene was firstly amplified from the genome of the *E. coli* K12 wild-type strain W3110 (Bachmann, B. J. (1972), Bacteriol. Rev. 36, 525–557) by the polymerase chain reaction (PCR). The known base sequence of the gene (Bardwell, J. C. A., McGovern, K. & Beckwith, J., "Identification of a Protein Required for Disulfide Bond Formation in vivo", Cell, 67, (1991), 581–589) served as a starting point for planning the corresponding oligonucleotide primers.

The following oligonucleotides were used as primers for the amplification of the PDI gene:

N-terminal primer: (SEQ ID NO: 4) 5'TTGCAATTAA-CAAAGCTTGAATTCTCGGAGAGAGTA-GATCATGAAAAAGAT3'

C-terminal primer: (SEQ ID NO: 5) 5'GGGCTTTATG-TAAAGCTTGGATCCTTATTTTTCTCG-GACAGATATTTC3'

The amplified DNA fragment which contains the complete PDI gene, including the signal sequence and ribosomal binding site, was isolated and cleaved with the restriction enzymes HindIII and BamHI. The plasmid pRBIa1was digested with the same enzymes, the vector fragment was isolated and ligated with the PDI gene. The resulting plasmid pRBIa1-PDI contains the gene for OmpA/RBI and PDI as a dicistronic operon under the control of the lac promoter (FIG. 3). The complete nucleotide sequence of the plasmid is documented in SEQ ID NO: 1.

In order to analyse the effect of the coexpression and cosecretion of PDI, *E. coli* JM83 was transformed with the plasmid PRBI-PDI.

The culture and determination of the amounts of intracellular RBI formed was carried out as described in examples 3 and 4. The analysis showed that only when reduced glutathione is added at the same time does the coexpression and cosecretion of PDI result in an increase in yield that is considerably more than the observed increase in yield when glutathione is added alone while the sole expression of PDI has absolutely no effect on the amount of functional periplasmatic RBI (Table 3).

TABLE 3

Increase in expression of functional RBI by coexpression of PDI from *E. coli*

| Addition to the medium | mg/l · OD* | relative increase | mg/l* | relative increase |
|---|---|---|---|---|
| without addition | 0.08 | 1.0 | 0.38 | 1.0 |
| 5 mmol/l GSH | 0.37 | 4.6 | 1.65 | 4.3 |
| PDI | 0.08 | 1.0 | 0.39 | 1.0 |
| PDI + 1 mM GSH | 0.42 | 6.0 | 1.71 | 4.4 |
| PDI + 5 mM GSH | 0.97 | 13.7 | 4.33 | 11.1 |
| PDI + 10 mM GSH | 0.54 | 7.7 | 2.17 | 5.6 |
| PDI + 1 mM GSH + 0.5 mM GSSG | 0.38 | 5.4 | 2.00 | 5.1 |
| PDI + 5 mM GSH + 0.5 mM GSSG | 0.60 | 8.6 | 2.54 | 6.5 |
| PDI + 10 mM GSH + 0.5 mM GSSG | 0.46 | 6.6 | 1.93 | 4.9 |
| PDI + 0.5 mM GSSG | 0.10 | 1.4 | 0.57 | 1.5 |

*The yields of intracellular functional RBI are quoted in mg/l · OD, the volume yields in mg/l. The determination of the RBI activity was carried out by the trypsin inhibition test in the soluble fraction of the total cell extract (cf. example 3).

What is claimed is:

1. A process for increasing the formation of the natural protein conformation when disulfide bonded proteins are secreted by an *E.coli* host that contains a recombinant DNA coding for the secreted protein, comprising culturing the host in a suitable culture medium in the presence of oxygen under conditions suitable for the expression of the recombinant DNA, wherein said culture medium contains 0.1 to 20 mmol/l of one or more thiol reagents.

2. Process according to claim 1, wherein said culture medium contains 1 to 15 mmol/l of at least one thiol reagent.

3. Process according to claim 2, wherein said culture medium contains 3 to 12 mmol/l of at least one thiol reagent.

4. Process according to claim 1, wherein said thiol reagent is a reducing thiol reagent with SH groups.

5. Process according to claim 1, wherein said thiol reagent is a reducing thiol reagent with one SH group per molecule.

6. Process according to claim 5, wherein said thiol reagent is selected from the group consisting of glutathione (GSH), cysteine, N-acetylcysteine, cysteamine, β-mercaptoethanol and mixtures thereof.

7. Process according to claim 1, wherein said thiol reagent is a mixture of reducing thiol reagents with SH groups and oxidizing thiol reagents with disulfide groups.

8. Process according to claim 7, wherein the molar ratio of reducing to oxidizing thiol reagents is between 2:1 to 20:1.

9. Process according to claim 8, wherein the molar ratio is 5:1 to 10:1.

10. Process according to claim 7, wherein said thiol reagent is a mixture of reduced glutathione (GSH) and glutathione disulfide (GSSG).

11. Process according to claim 10, wherein the recombinant DNA coding for the secreted protein is in an operative linkage with a DNA fragment that codes for a signal peptide for secretion through inner bacterial membranes.

12. Process according to claim 11, wherein the signal peptide is derived from *E. coli* OmpA protein.

13. Process according to claim 1, wherein the recombinant DNA coding for the secreted protein is under the control of an inducible promoter.

14. Process according to claim 1, wherein said culture medium is a complete medium.

15. Process according to claim 14, wherein said complete medium is LB medium.

16. Process according to claim 1, wherein said culture medium has a pH value between 5 and 9.

17. Process according to claim 16, wherein said culture medium has a pH value between 6 and 8.

18. Process according to claim 1, further comprising adding at least one monosaccharide and/or oligosaccharide to the culture medium, wherein said monosaccharide and oligosaccharide cannot be metabolized by the host.

19. Process according to claim 18, wherein said monosaccharide and oligosaccharide is selected from the group consisting of sorbose, saccharose, raffinose and mixtures thereof.

20. Process according to claim 18, wherein the concentration of the monosaccharide and oligosaccharide in the culture medium is between 0.1 mol/l and 1 mol/l.

21. Process according to claim 20, wherein the concentration of the monosaccharide and oligosaccharide in the culture medium is between 0.3 mol/l and 0.7 mol/l.

22. Process according to claim 1, further comprising overexpressing a protein disulfide isomerase gene while expressing the recombinant DNA which codes for the secreted disulfide-bonded protein, wherein said protein disulfide isomerase gene is compatible with *E. coli*.

23. Process according to claim 22, wherein said protein disulfide isomerase gene is a gram-negative bacteria protein disulfide isomerase gene.

24. Process according to claim 23, wherein said protein disulfide isomerase gene is an *E. coli* protein disulfide isomerase gene.

25. Process according to claim 22, wherein the protein disulfide isomerase gene is under the control of an inducible promoter.

26. Process according to claim 22, wherein the recombinant DNA coding for the protein to be secreted and the protein disulfide isomerase gene are present on a single extrachromosomal expression vector.

27. Process according to claim 26, wherein the recombinant DNA and the protein disulfide isomerase gene are under the control of a single promoter.

28. Process according to claim 22, wherein the recombinant DNA coding for the protein to be secreted and the protein disulfide isomerase gene are present on two mutually compatible extrachromosomal expression vectors.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 4690 base pairs
       (B) TYPE: nucleic acid
       (C) STRANDEDNESS: double
       (D) TOPOLOGY: circular (ix) FEATURE:
       (A) NAME/KEY: sig_peptide
       (B) LOCATION: 1328..1391

(ix) FEATURE:
       (A) NAME/KEY: mat_peptide
       (B) LOCATION: 1392..1756

(ix) FEATURE:
       (A) NAME/KEY: sig_peptide
       (B) LOCATION: 1789..1845

(ix) FEATURE:
       (A) NAME/KEY: mat_peptide
       (B) LOCATION: 1846..2412

(xi) SEQUENCE DESCRIPTION: SEQ ID NO:1:

```
ACCCGACACC ATCGAATGGC GCAAAACCTT TCGCGGTATG GCATGATAGC GCCCGGAAGA      60
GAGTCAATTC AGGGTGGTGA ATGTGAAACC AGTAACGTTA TACGATGTCG CAGAGTATGC     120
CGGTGTCTCT TATCAGACCG TTTCCCGCGT GGTGAACCAG GCCAGCCACG TTTCTGCGAA     180
AACGCGGGAA AAAGTGGAAG CGGCGATGGC GGAGCTGAAT TACATTCCCA ACCGCGTGGC     240
ACAACAACTG GCGGGCAAAC AGTCGTTGCT GATTGGCGTT GCCACCTCCA GTCTGGCCCT     300
GCACGCGCCG TCGCAAATTG TCGCGGCGAT TAAATCTCGC GCCGATCAAC TGGGTGCCAG     360
CGTGGTGGTG TCGATGGTAG AACGAAGCGG CGTCGAAGCC TGTAAAGCGG CGGTGCACAA     420
TCTTCTCGCG CAACGCGTCA GTGGGCTGAT CATTAACTAT CCGCTGGATG ACCAGGATGC     480
CATTGCTGTG AAGCTGCCT GCACTAATGT TCCGGCGTTA TTTCTTGATG TCTCTGACCA     540
GACACCCATC AACAGTATTA TTTTCTCCCA TGAAGACGGT ACGCGACTGG GCGTGGAGCA     600
TCTGGTCGCA TTGGGTCACC AGCAAATCGC GCTGTTAGCG GGCCCATTAA GTTCGTCTC     660
GGCGCGTCTG CGTCTGGCTG GCTGGCATAA ATATCTCACT CGCAATCAAA TTCAGCCGAT     720
AGCGGAACGG GAAGGCGACT GGAGTGCCAT GTCCGGTTTT CAACAAACCA TGCAAATGCT     780
GAATGAGGGC ATCGTTCCCA CTGCGATGCT GGTTGCCAAC GATCAGATGG CGCTGGGCGC     840
AATGCGCGCC ATTACCGAGT CCGGGCTGCG CGTTGGTGCG GATATCTCGG TAGTGGGATA     900
CGACGATACC GAAGACAGCT CATGTTATAT CCCGCCGTTA ACCACCATCA AACAGGATTT     960
TCGCCTGCTG GGGCAAACCA GCGTGGACCG CTTGCTGCAA CTCTCTCAGG GCCAGGCGGT    1020
GAAGGGCAAT CAGCTGTTGC CCGTCTCACT GGTGAAAAGA AAAACCACCC TGGCGCCCAA    1080
TACGCAAACC GCCTCTCCCC GCGCGTTGGC CGATTCATTA ATGCAGCTGG CACGACAGGT    1140
TTCCCGACTG GAAAGCGGGC AGTGAGCGCA ACGCAATTAA TGTGAGTTAG CTCACTCATT    1200
AGGCACCCCA GGCTTTACAC TTTATGCTTC CGGCTCGTAT GTTGTGTGGA ATTGTGAGCG    1260
GATAACAATT TCACACAGGA AACAGCTATG ACCATGATTA CGAATTTCTA GATAACGAGG    1320
GCAAAAAATG AAAAAGACAG CTATCGCGAT TGCAGTGGCA CTGGCCGGCT TCGCTACCGT    1380
```

-continued

```
AGCGCAGGCC TCTGTTGGTA CCTCTTGCAT CCCGGGTATG GCTATCCCGC ACAACCCACT   1440

GGACTCTTGT AGATGGTATG TGTCGACCCG CACCTGCGGG GTTGGCCCTA GACTGGCTAC   1500

TCAAGAAATG AAAGCTCGTT GCTGCCGTCA GCTCGAGGCT ATCCCGGCGT ACTGTCGTTG   1560

CGAAGCTGTT CGTATCCTGA TGGACGGTGT TGTGACGTCT TCTGGTCAGC ACGAAGGTCG   1620

TCTCCTGCAG GATCTCCCAG GTTGCCCGCG TCAGGTACAG CGTGCTTTCG CTCCGAAACT   1680

GGTTACTGAA GTTGAATGCA ACCTGGCGAC TATCCATGGT GGCCCGTTCT GCCTGTCTCT   1740

GCTGGGTGCT GGTGAATGAT AAGCTTGAAT TCTCGGAGAG AGTAGATCAT GAAAAAGATT   1800

TGGCTGGCGC TGGCTGGTTT AGTTTTAGCG TTTAGCGCAT CGGCGGCGCA GTATGAAGAT   1860

GGTAAACAGT ACACTACCCT GGAAAAACCG GTAGCTGGCG CGCCGCAAGT GCTGGAGTTT   1920

TTCTCTTTCT TCTGCCCGCA CTGCTATCAG TTTGAAGAAG TTCTGCATAT TTCTGATAAT   1980

GTGAAGAAAA AACTGCCGGA AGGCGTGAAG ATGACTAAAT ACCACGTCAA CTTCATGGGT   2040

GGTGACCTGG GCAAAGATCT GACTCAGGCA TGGGCTGTGG CGATGGCGCT GGGCGTGGAA   2100

GACAAAGTGA CTGTTCCGCT GTTTGAAGGC GTACAGAAAA CCCAGACCAT TCGTTCTGCT   2160

TCTGATATCC GCGATGTATT TATCAACGCA GGTATTAAAG GTGAAGAGTA CGACGCGGCG   2220

TGGAACAGCT TCGTGGTGAA ATCTCTGGTC GCTCAGCAGG AAAAAGCTGC AGCTGACGTG   2280

CAATTGCGTG GCGTTCCGGC GATGTTTGTT AACGGTAAAT ATCAGCTGAA TCCGCAGGGT   2340

ATGGATACCA GCAATATGGA TGTTTTTGTT CAGCAGTATG CTGATACAGT GAAATATCTG   2400

TCCGAGAAAA AATAAGGATC CCCACGCGCC CTGTAGCGGC GCATTAAGCG CGGCGGGTGT   2460

GGTGGTTACG CGCAGCGTGA CCGCTACACT TGCCAGCGCC CTAGCGCCCG CTCCTTTCGC   2520

TTTCTTCCCT TCCTTTCTCG CCACGTTCGC CGGCTTTCCC CGTCAAGCTC TAAATCGGGG   2580

CATCCCTTTA GGGTTCCGAT TTAGTGCTTT ACGGCACCTC GACCCCAAAA AACTTGATTA   2640

GGGTGATGGT TCACGTAGTG GGCCATCGCC CTGATAGACG GTTTTTCGCC CTTTGACGTT   2700

GGAGTCCACG TTCTTTAATA GTGGACTCTT GTTCCAAACT GGAACAACAC TCAACCCTAT   2760

CTCGGTCTAT TCTTTTGATT TATAAGGGAT TTTGCCGATT TCGGCCTATT GGTTAAAAAA   2820

TGAGCTGATT TAACAAAAAT TTAACGCGAA TTTTAACAAA ATATTAACGT TTACAATTTC   2880

AGGTGGCACT TTTCGGGGAA ATGTGCGCGG AACCCCTATT TGTTTATTTT TCTAAATACA   2940

TTCAAATATG TATCCGCTCA TGAGACAATA ACCCTGATAA ATGCTTCAAT AATATTGAAA   3000

AAGGAAGAGT ATGAGTATTC AACATTTCCG TGTCGCCCTT ATTCCCTTTT TTGCGGCATT   3060

TTGCCTTCCT GTTTTTGCTC ACCCAGAAAC GCTGGTGAAA GTAAAAGATG CTGAAGATCA   3120

GTTGGGTGCA CGAGTGGGTT ACATCGAACT GGATCTCAAC AGCGGTAAGA TCCTTGAGAG   3180

TTTTCGCCCC GAAGAACGTT TTCCAATGAT GAGCACTTTT AAAGTTCTGC TATGTGGCGC   3240

GGTATTATCC CGTATTGACG CCGGGCAAGA GCAACTCGGT CGCCGCATAC ACTATTCTCA   3300

GAATGACTTG GTTGAGTACT CACCAGTCAC AGAAAAGCAT CTTACGGATG CATGACAGT   3360

AAGAGAATTA TGCAGTGCTG CCATAACCAT GAGTGATAAC ACTGCGGCCA ACTTACTTCT   3420

GACAACGATC GGAGGACCGA AGGAGCTAAC CGCTTTTTTG CACAACATGG GGATCATGT   3480

AACTCGCCTT GATCGTTGGG AACCGGAGCT GAATGAAGCC ATACCAAACG ACGAGCGTGA   3540

CACCACGATG CCTGTAGCAA TGGCAACAAC GTTGCGCAAA CTATTAACTG GCGAACTACT   3600

TACTCTAGCT TCCCGGCAAC AATTAATAGA CTGGATGGAG GCGGATAAAG TTGCAGGACC   3660

ACTTCTGCGC TCGGCCCTTC CGGCTGGCTG GTTTATTGCT GATAAATCTG GAGCCGGTGA   3720
```

-continued

```
GCGTGGGTCT CGCGGTATCA TTGCAGCACT GGGGCCAGAT GGTAAGCCCT CCCGTATCGT      3780

AGTTATCTAC ACGACGGGGA GTCAGGCAAC TATGGATGAA CGAAATAGAC AGATCGCTGA      3840

GATAGGTGCC TCACTGATTA AGCATTGGTA ACTGTCAGAC CAAGTTTACT CATATATACT      3900

TTAGATTGAT TTAAAACTTC ATTTTTAATT TAAAAGGATC TAGGTGAAGA TCCTTTTTGA      3960

TAATCTCATG ACCAAAATCC CTTAACGTGA GTTTTCGTTC CACTGAGCGT CAGACCCCGT      4020

AGAAAAGATC AAAGGATCTT CTTGAGATCC TTTTTTTCTG CGCGTAATCT GCTGCTTGCA      4080

AACAAAAAAA CCACCGCTAC CAGCGGTGGT TTGTTTGCCG GATCAAGAGC TACCAACTCT      4140

TTTTCCGAAG GTAACTGGCT TCAGCAGAGC GCAGATACCA AATACTGTCC TTCTAGTGTA      4200

GCCGTAGTTA GGCCACCACT TCAAGAACTC TGTAGCACCG CCTACATACC TCGCTCTGCT      4260

AATCCTGTTA CCAGTGGCTG CTGCCAGTGG CGATAAGTCG TGTCTTACCG GGTTGGACTC      4320

AAGACGATAG TTACCGGATA AGGCGCAGCG GTCGGGCTGA ACGGGGGGTT CGTGCACACA      4380

GCCCAGCTTG GAGCGAACGA CCTACACCGA ACTGAGATAC CTACAGCGTG AGCTATGAGA      4440

AAGCGCCACG CTTCCCGAAG GGAGAAAGGC GGACAGGTAT CCGGTAAGCG GCAGGGTCGG      4500

AACAGGAGAG CGCACGAGGG AGCTTCCAGG GGGAAACGCC TGGTATCTTT ATAGTCCTGT      4560

CGGGTTTCGC CACCTCTGAC TTGAGCGTCG ATTTTTGTGA TGCTCGTCAG GGGGGCGGAG      4620

CCTATGGAAA AACGCCAGCA ACGCGGCCTT TTTACGGTTC CTGGCCTTTT GCTGGCCTTT      4680

TGCTCACATG                                                            4690
```

(2) INFORMATION FOR SEQ ID NO:2:

(i) SEQUENCE CHARACTERISTICS:
        (A) LENGTH: 460 base pairs
        (B) TYPE: nucleic acid
        (C) STRANDEDNESS: double
        (D) TOPOLOGY: circular (ix) FEATURE:
        (A) NAME/KEY: sig_peptide
        (B) LOCATION: 22..85

(ix) FEATURE:
        (A) NAME/KEY: mat_peptide
        (B) LOCATION: 86..451

(xi) SEQUENCE DESCRIPTION: SEQ ID NO:2:

```
TCTAGATAAC GAGGGCAAAA AATGAAAAAG ACAGCTATCG CGATTGCAGT GGCACTGGCC       60

GGCTTCGCTA CCGTAGCGCA GGCCTCTGTT GGTACCTCTT GCATCCCGGG TATGGCTATC      120

CCGCACAACC CACTGGACTC TTGTAGATGG TATGTGTCGA CCCGCACCTG CGGGGTTGGC      180

CCTAGACTGG CTACTCAAGA AATGAAAGCT CGTTGCTGCC GTCAGCTCGA GGCTATCCCG      240

GCGTACTGTC GTTGCGAAGC TGTTCGTATC CTGATGGACG GTGTTGTGAC GTCTTCTGGT      300

CAGCACGAAG GTCGTCTCCT GCAGGATCTC CCAGGTTGCC CGCGTCAGGT ACAGCGTGCT      360

TTCGCTCCGA AACTGGTTAC TGAAGTTGAA TGCAACCTGG CGACTATCCA TGGTGGCCCG      420

TTCTGCCTGT CTCTGCTGGG TGCTGGTGAA TGATAAGCTT                            460
```

(2) INFORMATION FOR SEQ ID NO:3:

(i) SEQUENCE CHARACTERISTICS:
        (A) LENGTH: 639 base pairs
        (B) TYPE: nucleic acid
        (C) STRANDEDNESS: double
        (D) TOPOLOGY: circular (ix) FEATURE:

-continued

```
         (A) NAME/KEY: sig_peptide
         (B) LOCATION: 16..72

(ix) FEATURE:
         (A) NAME/KEY: mat_peptide
         (B) LOCATION: 73..639

(xi) SEQUENCE DESCRIPTION: SEQ ID NO:3:

CGGAGAGAGT AGATCATGAA AAAGATTTGG CTGGCGCTGG CTGGTTTAGT TTTAGCGTTT     60

AGCGCATCGG CGGCGCAGTA TGAAGATGGT AAACAGTACA CTACCCTGGA AAAACCGGTA    120

GCTGGCGCGC CGCAAGTGCT GGAGTTTTTC TCTTTCTTCT GCCCGCACTG CTATCAGTTT    180

GAAGAAGTTC TGCATATTTC TGATAATGTG AAGAAAAAAC TGCCGGAAGG CGTGAAGATG    240

ACTAAATACC ACGTCAACTT CATGGGTGGT GACCTGGGCA AAGATCTGAC TCAGGCATGG    300

GCTGTGGCGA TGGCGCTGGG CGTGGAAGAC AAAGTGACTG TTCCGCTGTT TGAAGGCGTA    360

CAGAAAACCC AGACCATTCG TTCTGCTTCT GATATCCGCG ATGTATTTAT CAACGCAGGT    420

ATTAAAGGTG AAGAGTACGA CGCGGCGTGG AACAGCTTCG TGGTGAAATC TCTGGTCGCT    480

CAGCAGGAAA AAGCTGCAGC TGACGTGCAA TTGCGTGGCG TTCCGGCGAT GTTTGTTAAC    540

GGTAAATATC AGCTGAATCC GCAGGGTATG GATACCAGCA ATATGGATGT TTTTGTTCAG    600

CAGTATGCTG ATACAGTGAA ATATCTGTCC GAGAAAAAA                            639

(2) INFORMATION FOR SEQ ID NO:4:

(i) SEQUENCE CHARACTERISTICS:
         (A) LENGTH: 51 base pairs
         (B) TYPE: nucleic acid
         (C) STRANDEDNESS: single
         (D) TOPOLOGY: linear (xi) SEQUENCE DESCRIPTION: SEQ ID NO:4:

TTGCAATTAA CAAAGCTTGA ATTCTCGGAG AGAGTAGATC ATGAAAAAGA T              51

(2) INFORMATION FOR SEQ ID NO:5:

(i) SEQUENCE CHARACTERISTICS:
         (A) LENGTH: 49 base pairs
         (B) TYPE: nucleic acid
         (C) STRANDEDNESS: single
         (D) TOPOLOGY: linear (xi) SEQUENCE DESCRIPTION: SEQ ID NO:5:

GGGCTTTATG TAAAGCTTGG ATCCTTATTT TTTCTCGGAC AGATATTTC                 49
```